United States Patent [19]

Schmidt et al.

[11] Patent Number: 4,969,878
[45] Date of Patent: Nov. 13, 1990

[54] THICK-WALLED FLEXIBLE PROBE FOR INSERTION IN THE TRACHEA OR RESPECTIVELY IN THE BRONCHIAL SYSTEM

[76] Inventors: Christoph Schmidt, Am Kumpel 12; Rudolf Schön, Am Kumpel 18; Jurgen Russ, Rosental 32, all of, 5300 Bonn 1, Fed. Rep. of Germany

[21] Appl. No.: 273,815
[22] PCT Filed: Jul. 10, 1986
[86] PCT No.: PCT/DE86/00283
    § 371 Date: Sep. 19, 1988
    § 102(e) Date: Sep. 19, 1988
[87] PCT Pub. No.: WO87/05522
    PCT Pub. Date: Sep. 24, 1987

[30] Foreign Application Priority Data

Mar. 18, 1986 [DE] Fed. Rep. of Germany ....... 3608943

[51] Int. Cl.⁵ .............................................. A61M 25/00
[52] U.S. Cl. ...................................... 604/264; 604/280
[58] Field of Search .................................. 604/43-45, 604/267-268, 280, 119, 902, 264; 128/207.14, 207.15

[56] References Cited

U.S. PATENT DOCUMENTS

| 3,430,631 | 3/1969 | Abramson. | |
|---|---|---|---|
| 3,848,604 | 11/1974 | Sackner | 604/119 |
| 4,300,550 | 11/1981 | Gandi et al. . | |
| 4,344,436 | 8/1982 | Kubota | 128/207.15 X |
| 4,468,216 | 8/1984 | Muto | 604/43 |
| 4,488,548 | 12/1984 | Agdanowski | 128/207.15 X |
| 4,669,463 | 6/1987 | McConnell | 128/207.14 |
| 4,735,606 | 4/1988 | Davison | 604/45 X |

FOREIGN PATENT DOCUMENTS

| 0098688A | 1/1984 | European Pat. Off. . | |
|---|---|---|---|
| 2308400 | 8/1974 | Fed. Rep. of Germany . | |
| 2540536 | 4/1976 | Fed. Rep. of Germany . | |
| 2736771 | 2/1978 | Fed. Rep. of Germany . | |
| 2364119 | 10/1978 | Fed. Rep. of Germany . | |
| 2847681 | 5/1980 | Fed. Rep. of Germany . | |
| 3127249 | 6/1982 | Fed. Rep. of Germany . | |
| 3327586 | 2/1984 | Fed. Rep. of Germany . | |
| 3506738 | 10/1985 | Fed. Rep. of Germany . | |
| 808085 | 3/1981 | U.S.S.R. | 604/45 |
| 1301393 | 12/1972 | United Kingdom . | |
| 2079609 | 1/1982 | United Kingdom . | |

OTHER PUBLICATIONS

Schmidt, C. et al., *New Endobronchial Tube for Administration of Drugs During Resuscitation*, [Notfall/Medizin, vol. 14, 1988, pp. 673–677].

Primary Examiner—John D. Yasko
Assistant Examiner—Adam J. Cermak
Attorney, Agent, or Firm—Antonelli, Terry, Stout & Kraus

[57] ABSTRACT

Tubular flexible probe for insertion in the wind-pipe or in the bronchial system, in particular for use as a suction catheter with a tube (10) having an outside diameter of roughly 5–8 mm and a length of roughly 30–50 cm. Its end, which can be inserted in the wind-pipe or in the bronchial system can be designed as an annular collar (12) and in the region of the annular collar may have holes (21) with at least one channel (2) having a diameter of about 1 to a maximum of 2 mm for the conveyance of medicaments. Its inlet (23) is provided with a connection piece (3) for attahcment of a syringe.

7 Claims, 3 Drawing Sheets

THICK-WALLED FLEXIBLE PROBE FOR INSERTION IN THE TRACHEA OR RESPECTIVELY IN THE BRONCHIAL SYSTEM

The invention relates to a tubular flexible probe for insertion in the trachea or, respectively, in the bronchial system, especially for use as a suction catheter, with a duct formed by a tube having a length of about 30 to 50 cm and an outer diameter of about 5 to 8 mm, the end of this duct, which can be introduced into the bronchial system, being fashioned optionally as an annular collar and, if desired, exhibiting vent holes in the zone in front of the annular collar.

Probes of the type described above, as known, for example, from DAS No. 2,364,119, are utilized for removing, by suction, mucus and water from the lungs and the trachea. The tubular flexible catheter has an outer diameter of about 5–8 mm with an internal diameter for the suction duct of about 3.5–6 mm. The annular collar formed at the end introduced into the bronchial system facilitates introduction and prevents adherence by suction and injuries to the mucous membrane and the bronchi. Such catheters are intended for one-time, short-term usage.

Efforts have been made in recent times to introduce medicaments directly into the lung of the affected person in the treatment of emergencies. When using the conventional suction catheters for this purpose, there is the grave disadvantage that the medicaments must be introduced, after aspiration, through the suction duct and pass down into the lungs only in minor proportions on account of the size of the duct, while they otherwise remain in the catheter tube. The objective of introducing the medicaments completely and deeply into the lung and to distribute them therein is not achieved. Also, the known catheters are not equipped with attachments for fitting a syringe.

For respiration and oxygenation, so-called respirator tubes or balloon catheters are known for long-term usage; these are introduced only into the trachea and are unsuited for use as suction catheters since their open, beveled end would lead to considerable injuries to the bronchial tissue. In the respirator tube according to DOS No. 2,308,400, suction removal is to be made possible besides providing respiration, and for this purpose a catheter is guided coaxially through the tube, reducing and impeding the tube cross section. This is of no consequence in respiration, but presents a drawback in aspiration of the bronchi and lungs through this tube inasmuch as clogging of the cross section can occur. Furthermore, in case of the respirator tube according to DOS No. 2,308,400, aspiration can be performed only intermittently during exhaling. Irrigation and simultaneous suctioning off of secretions is impossible with the respirator tube according to DOS No. 2,308,400 since, with the irrigation fluid being supplied via the catheter, suction will have to be effected via the tube. As a consequence, the respirator tube would adhere by suction to the bifurcation, resulting in diffuse, gravest hemorrhaging with highest danger to life. The necessary respiration and, respectively, oxygen exchange cannot be performed simultaneously during irrigation and suctioning.

The invention is based on the object of providing a probe or a catheter with which medicaments can be introduced through the trachea and, respectively, bronchi to deeply into the bronchial system and, respectively, the lungs, optionally in conjunction with aspiration.

The invention attains the thus-posed object by means of a tubular flexible probe suitable for introduction into the trachea or, respectively, the bronchial system, by providing that the tube exhibits at least one duct having a diameter of about 1 mm up to maximally about 2 mm for passing medicaments and/or irrigation solution therethrough, the inlet of which tube can be equipped with an attachment for connecting a syringe, and the outlet of which terminates within the tube or at the tube end.

The invention is based on the realization that a maximally high pressure difference is required between the ends of the probe in order to obtain thereby a high flow rate for the deep introduction and distribution of medicaments into the lung. For this purpose, very small duct cross sections are necessary along the lines of the invention. A hose having such a small duct diameter exhibits, in case the wall thickness is of normal design, an outer diameter which is not much larger and therefore is so flexible that it can no longer be perfectly introduced into the bronchial system.

The invention is based on a probe suitable for introduction into the bronchial system with external dimensions of a size and configuration as known for the suction removal of mucus and water from the lungs, and such a probe is fashioned, in accordance this invention, with a duct having such a small cross section that a high pressure difference is made possible for the deep introduction of medicaments into the lung at a high flow rate. At the same time, the inlet of this medicament duct is equipped with a connecting piece for the attachment of a syringe; the connecting piece can be designed as a separate component or can be fashioned integrally with the tube or, respectively, the duct.

The probe can be fashioned in accordance with the invention so that it permits either solely the introduction of medicaments by means of a single, small duct present—medicine duct or administering duct—or the alternative introduction of medicaments through the administering duct and aspiration through the second duct, i.e. the aspiration duct. In case the probe is to serve exclusively for the administration of medicines, then the probe can be fashioned, according to a suggestion of this invention, so that the administering duct extends within the large duct of the tube and is constituted, for example, by a hose arranged in the large duct. The outer diameter of the hose must in any event be smaller than the inner diameter of the large duct. Preferably, the hose inserted in the tube should have an outer diameter of about 2 mm. The hose is likewise manufactured from a flexible, supple, sterilizable material, e.g. a synthetic resin. The hose must be equipped in its inlet zone with an attachment for a syringe connected to the inlet zone of the large duct of the tube. For example, the attachment or connecting piece can be manufactured integrally with the tube or hose, i.e. it can be of one piece therewith. The attachment herein serves for the placement of a syringe for introducing medicaments; in this connection, the attachment can also be additionally provided, for example, with a valve or a closure means.

It is also possible to fashion the probe according to this invention with a tube having an outer diameter of about 5 mm to 8 mm and with only a single, very small duct having a diameter of about 1–2 mm solely for passing therethrough medicaments at a high flow rate.

The size of the tube takes care of the perfect introduction into the bronchial system. The attachment for the syringe can be molded directly at the tube end—fashioned integrally with a continuous duct or bore. The tube is distinguished by a relatively large wall thickness of at least about 1.5 mm. Only very supple, soft, flexible plastics can then be utilized for this purpose. In these probes of a structure in accordance with the invention, the tube end to be introduced into the trachea can also be designed to taper in a rounded fashion, in place of an annular collar. In particular, it is also possible to arrange the outlet of the small administering duct on the jacket surface of the tube in the zone of the tube end.

For using the probe in accordance with this invention alternatingly as a suction catheter and for the administration of medicaments and/or irrigation solution, it is proposed that the tube exhibit two parallel-juxtaposed ducts of differing diameters, wherein the duct having a diameter of about 1 to 2 mm in all cases is the duct with the smaller diameter.

In accordance with this version of the invention, the large duct of the probe serves for the aspiration of mucus, and the additional duct having the very much smaller diameter serves for the introduction of medicaments directly down into the lung. The medicaments are injected by way of a syringe into this small duct wherein a high pressure can be built up so that the medicaments are injected deeply into the lung and at the same time are satisfactorily distributed. The second duct can terminate either still within the tube upstream of the tube end or alternatively flush with the end of the tube. The tube, in all probes, has a length of about 30–50 cm; it is made of a supple, flexible and sterilizable material, e.g. a synthetic resin. The tube can have an outer diameter of about 5–8 mm, the duct diameter for suction removal of mucus being about 3–4 mm. The duct for introducing the medicaments into the lungs should have an inside diameter of about 1–1½ mm up to maximally 2 mm.

Also this probe preferably exhibits an annular collar at the end introducible into the bronchial system in order to facilitate insertion and can be fashioned with lateral openings at the tube in the proximity of the annular collar, preventing adherence due to suction at the mucous membranes. An advantageous embodiment of the probe with two ducts extending in side-by-side relationship provides that the wall of the tube defining the duct with the smaller diameter exhibits a recess in the region of the inlet end of the tube through which a connecting hose equipped with an attachment for a syringe is extended into the duct or is connected to the latter. A connecting piece for aspiration can be inserted, for example stuck into the inlet end of the tube into the large duct. The connecting pieces for suction removal can be fashioned with a valve or a closure means. A probe equipped according to this invention with two ducts running side-by-side for introduction into the bronchial system can be utilized in such a way that either solely medicaments are introduced or, alternatively, aspiration is performed through the large duct and then, alternatingly, irrigation solution or medicaments are introduced into the lung through the small duct.

The connecting pieces for the syringes are advantageously equipped with a closure means, such as a valve, a plug, a hinged cover. Furthermore, it is possible in accordance with a further proposal of the invention to equip the tube wall in the axial longitudinal extension with an X-ray contrast strip. Accordingly, control by X-rays is possible during the treatment.

By means of the invention, a considerable advance in the art of the treatment of patients is attained in the medical field here under consideration. Heretofore, it has merely been possible during resuscitation to operate with the appliances present, in the following sequence:

(1) Introduction of a respirator tube into the trachea.
(2) Introduction of irrigation solution into the respirator tube.
(3) Ventilation with a respirator bag for distribution of the irrigation fluid.
(4) Introduction of a suction catheter with exclusive suctioning.
(5) Removal of suction catheter.
(6) Introduction of a cava catheter, incurring the dangers of injury to the mucous membrane (stopgap solution).
(7) Introduction of emergency medicaments via the cava catheter.
(8) Removal of cava catheter.
(9) Initiation of volume-controlled respiration.

The time required for this purpose is, in total, about 3 to 3½ minutes.

With this therapy, damage due to lack of oxygen supply to the emergency patient cannot be excluded. Also, adequate administration of the emergency medicaments through the cava catheter is not always ensured. In addition, there is the large amount of material consumed, requiring a lot of labor and being uneconomical.

The invention makes it possible to take care of the emergency patient as follows:

(1) Introduction of the respirator tube into the trachea.
(2) Introduction of the probe, fashioned as an irrigation and suction catheter, by way of the trachea.
(3) Simultaneous irrigation and aspiration of the bronchial tract by means of the probe.
(4) Subsequent deep administration of emergency medicaments by means of the probe into the lung.
(5) Removal of the probe.
(6) Initiation of volume-controlled respiration by means of the respiration tube.

Duration of the entire treatment is 30 seconds to 1 minute.

By use of this invention, a substantially faster treatment of the emergency patient is made possible, considerably raising chance of survival. Damage to the central nervous system can be reduced to the utmost minimum. Moreover, the labor to be expended in this procedure is substantially less, and so is the usage of material.

The invention is described in the drawing with the aid of examples but is not limited thereto.

In the drawing, in schematic representation:

Figure 1:
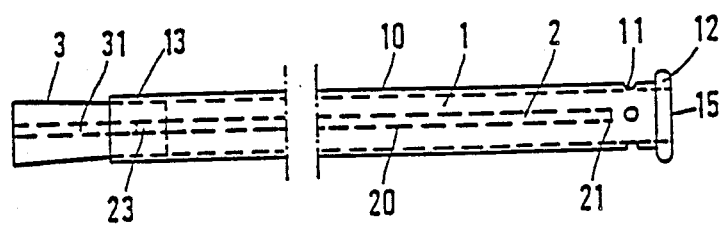
FIG. 1 shows a view of a probe with a small duct solely for administration of medicaments arranged within the large duct.
Figure 2:
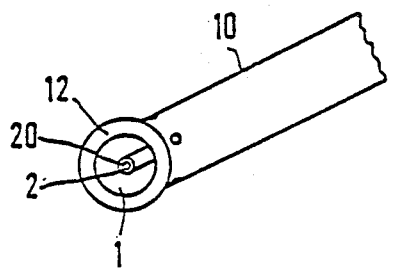
FIG. 2 is a plan view of the end of the probe according to FIG. 1.

The probe for introduction into the bronchial system, fashioned solely for the direct conveyance of medicaments into the lung, contains in accordance with FIG. 1 the outer tube 10. The tube 10 is manufactured, for example, from an inert synthetic resin hose and is flexible. The tube 10 is designed with the annular collar 12 at its end that can be introduced into the trachea. In the zone upstream of the annular collar 12, the tube 10 can exhibit holes 11. The tube 10 contains the continuous duct 1 having, for example, a diameter of about 3-4.5 mm. In case a coupling for an aspiration procedure is attached, for example, to the inlet end 13 of the tube 10, then such a tube 10 serves for the aspiration of mucus and water from the lung. In order to introduce medicaments into the lung, the tube 10 is then equipped with a further, very much smaller duct 2 located, for example, within the duct 1. The second, smaller duct is constituted, for example, by a hose 20 connected with the attachment 3 at the inlet end 23 by insertion in the continuous duct 31 of the attachment 3. It is also possible to fashion the attachment as early as during manufacture as an integral part of the hose end. The attachment 3 is inserted in the open inlet end 13 of the tube 10 in the duct 1, or firmly connected to the latter in some other way. It is also possible to fashion the attachment during the manufacture of the tube integrated therewith in one piece at the end. By way of the duct 31, it is possible by means of a syringe to inject a medicament solution into the lung through the small duct 2 extended within the tube 10 in the duct 1, upon introduction into the bronchial system. In this procedure, a high pressure difference is built up in the small duct 2 having a diameter of 1 up to maximally 2 mm; this pressure difference imparts to the medicament solution a high flow rate so that the solution is introduced deep into the lung and with fine distribution. The size of the outer dimensions of the tube 10 ensures that the hose 20 with the duct 2 can be readily introduced into the bronchial system. The hose end 21 can terminate still within the tube 10 or alternatively can end flush with the annular collar 12, i.e. with the tube end 15. FIG. 2 shows a perspective view of the end of the probe introducible into the trachea, according to FIG. 1. The probe of FIGS. 1 and 2 is utilized practically only for the introduction of medicaments directly into the lung by insertion of the probe in the bronchial system and injection of the medicaments by means of a syringe via the duct 2. On account of the firm outer tube 10 surrounding the hose 20 with the small duct 2, a perfect introduction of the hose 20 into the bronchial system is ensured.

Figure 3:
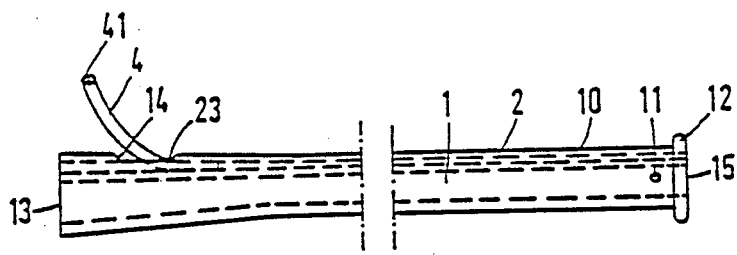
FIG. 3 is a view of a probe with two ducts extending in side-by-side relationship for administration and aspiration.
Figure 4:
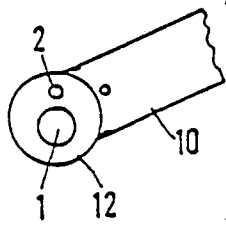
FIG. 4 is a plan view of the end of the probe according to FIG. 3.
Figure 5:
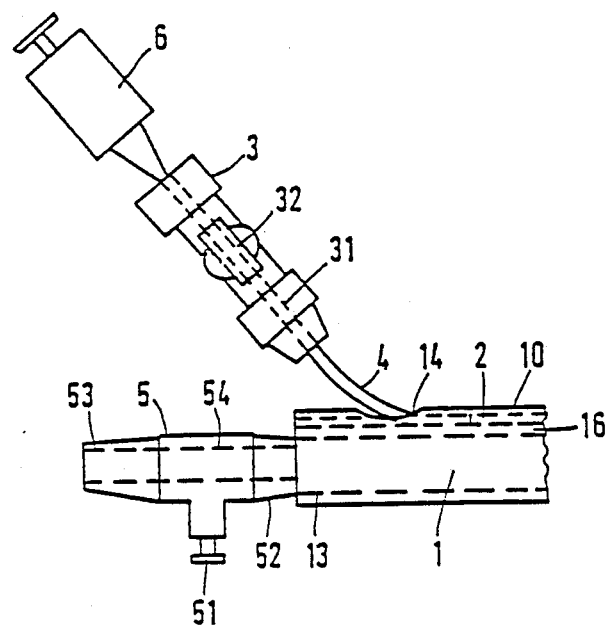
FIG. 5 shows the inlet end with a probe according to FIG. 3 with connections.

FIGS. 3-5 show another embodiment of a probe for the introduction of medicaments into the lung. According to FIG. 3, the outer tube 10, having an outer diameter of about 7 mm, is designed with two ducts 1, 2 extending in parallel in side-by-side relationship. At the end 15 of the tube 10 that can be introduced into the trachea, an annular collar 12 is molded thereto serving for facilitating the introduction of the probe into the trachea. In this arrangement, holes 11 should be provided in the wall of the tube in the region of the tube end upstream of the annular collar 12, which are to prevent adherence of the tube 10 by suction at the mucous membranes. The perspective view of the insertion end of the tube 10, i.e. the probe according to FIG. 4, likewise depicts the arrangement and configuration of the two ducts 1, 2 with differing diameters. The duct 1, having a diameter of about 3-8 mm, depending on the outer diameter of the tube, serves for the aspiration of secretions, water, and mucus from the lung whereas the very much smaller duct 2, having a diameter of about 1 to maximally 2 mm, serves for the introduction of medicaments or irrigation solutions into the lung. The probe according to FIG. 2 represents a double-lumen catheter for the intrabronchial aspiration of secretion and administration of medicaments and/or irrigation solutions. A connection for aspiration can be attached, for example, to the inlet end 13 of the large duct 1 of the probe according to FIG. 3. For connecting the small duct 2 according to FIG. 3, the recess 14 is formed in the wall of the tube in the zone of the inlet end 13 of the tube 10, through which recess a connection, e.g. in the shape of a hose piece 4, can be introduced into the inlet 23 of the duct, or is fixedly joined to the latter. At the end 41, the attachment for a syringe can be connected to the elastic hose piece 4, or such attachment can be formed directly integrally with the hose end 41 so that the medicaments can be introduced via the attachment and the hose 4 into the duct 2 and thus through the trachea into the lung. The duct 1 and the duct 2 are bulkheaded with respect to each other by the partition 16.

Thus, by means of the probes of a structure according to this invention, it is possible during emergency treatment of human patients to administer medicaments deeply and safely into the bronchial system and into the lung, and in the same operating step, in case of the design with ducts extending in parallel side-by-side, mucus and secretions can be suctioned off beforehand.

In the usage of the double-lumen probe according to the invention, irrigation and aspiration can also be performed while respirating is carried out, i.e. without disconnection of a respirator unit via the access of a right-angle, dual rotary connector at the tube.

FIG. 5 shows schematically the connection and structure of connecting pieces 5 for the aspiration procedure and of attachments 3 for the syringes 6 of a probe according to FIGS. 3 and 4. At the inlet end 13 into the duct 1 of the tube 10, the connecting piece 5 is inserted with the conical end 52. The attachment 5 exhibits the continuous bore 54 which can be closed by means of the valve 51. For attaching an aspirator, the connecting piece 5 furthermore exhibits the conical tap 53.

For the introduction of medicaments or irrigation solutions by means of a syringe 6 into the duct 2, the free hose end 4 is equipped with the attachment 3. The attachment 3 has the continuous bore 31 sealable by means of a valve 32, designed as a three-way cock, for example. One end of the attachment 3 is connected to the hose end 4 while, at the other end, the syringe 6 can be inserted in the bore 31. Also other attachments can be utilized.

Figure 9:
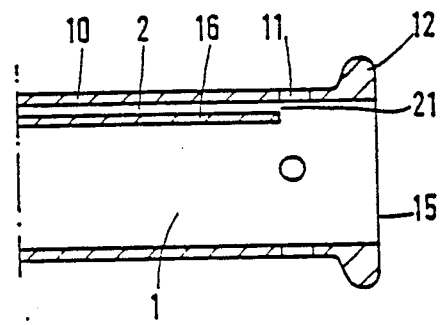
FIG. 9 is a fragmentary longitudinal section through a double-lumen probe.

FIG. 9 shows, in a fragmentary cross section, the structure of the end 15 of a double-lumen probe, this probe exhibiting at the end the annular collar 12 and holes 11 and wherein the smaller duct 2 terminates within the tube 10, preferably still upstream of the holes 11, and at this point already passes into the duct 1. The partition 16 between the ducts 1, 2 ends upstream of the holes 11 in this embodiment.

Figure 6:
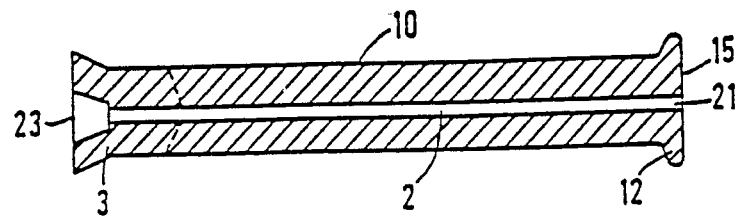
FIGS. 6-8 are longitudinal sectional views of various probes with respectively one duct for administration purposes.
Figure 7:
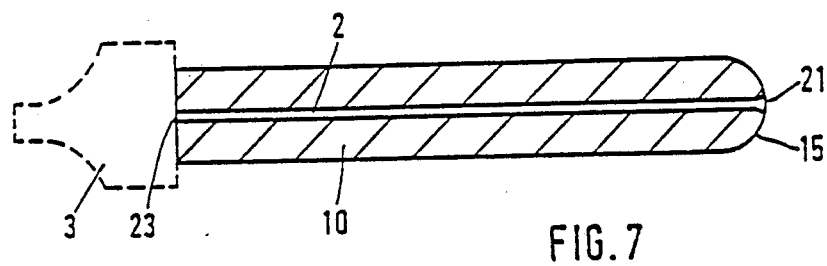
Figure 8:
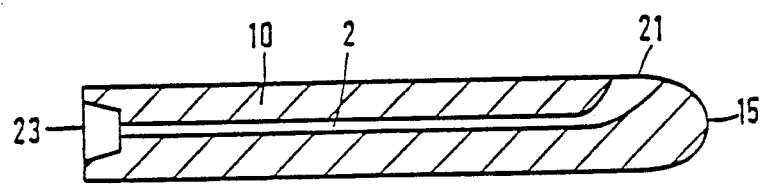

In FIGS. 6-8, various embodiments of probes of this invention with a lumen are illustrated, utilized as catheters for intrabronchial administration of medicaments.

In the probe according to FIG. 6, the attachment 3 for the syringe is formed integrally with the thick-walled tube 10, and the annular collar 12 is formed at the tube outlet 15. The small medicament duct 2 extends axially through the inlet 23 up to the outlet 21 at the tube end.

In the probe of FIG. 7, the tube end 15 tapers and the duct outlet 21 of the duct 2 is formed centrally at the tip, optionally slightly flaring in a nozzle shape. The attachment 3 for the syringe is placed on the tube.

In the probe according to FIG. 8, the tube end 15 likewise tapers in rounded fashion, but the outlet 21 of the duct 2 is provided laterally at the outer surface of the tube 10 in the zone of the tube end.

We claim:

1. A tubular flexible probe for introduction into the trachea and, respectively, into the bronchial system, which comprises a unitary tube made of synthetic resin extending along a longitudinal axis, having a length of about 30-50 cm and an outer diameter of about 5-8 mm, said tube having a continuous duct extending longitudinally along said axis through the tube from an inlet end to an outlet end; said duct having a diameter of about 1 mm up to maximally about 2 mm for passing medicaments and/or irrigation solution therethrough at a high flow rate and said tube having a wall thickness of at least 1.5 mm, with an outer diameter of the tube of 5 mm, and at least about 3 mm, with an outer diameter of 8 mm, and an attachment for connection of a syringe for the medicaments and/or irrigation solution being arranged at the inlet end of the duct; an end of the tube adjacent to the outlet end of the duct being tapered in a rounded fashion.

2. A probe according to claim 1, wherein the duct has a diameter of about 1 to 1.5 mm.

3. A probe according to claim 1 or claim 2, wherein the attachment is formed integrally with the inlet end of the duct.

4. A probe according to claim 1, wherein the outlet end of the duct is located on an outer surface of the tube.

5. A probe according to claim 1, wherein an outer surface of the wall of the tube is equipped in an axial longitudinal extension with an X-ray contrast strip.

6. A probe according to claim 1, wherein the outlet end of the duct flares outwardly.

7. A probe according to claim 1, wherein the attachment is provided with a closure means.

* * * * *